(12) United States Patent
Lange et al.

(10) Patent No.: US 6,387,099 B1
(45) Date of Patent: May 14, 2002

(54) SURGICAL CABLE CRIMP

(75) Inventors: Eric Lange, Germantown, TN (US); Michael Paul Lintell-Smith, East Norriton, PA (US)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/534,346

(22) Filed: Mar. 24, 2000

(51) Int. Cl.[7] .............................................. A61B 17/58
(52) U.S. Cl. ........................ 606/74; 606/103; 24/115 A
(58) Field of Search ..................... 606/74, 103, 151, 606/232; 24/115 R, 129 R, 129 W, 115 A, 131 R, 703.1; 140/105, 106; 248/317

(56) References Cited

U.S. PATENT DOCUMENTS

| | | | |
|---|---|---|---|
| 4,069,991 A | * 1/1978 | Saunders et al. | 248/317 |
| 4,262,391 A | 4/1981 | Peash | 24/18 |
| 4,966,600 A | 10/1990 | Songer et al. | 606/74 |
| 5,190,545 A | 3/1993 | Corsi et al. | 606/74 |
| 5,318,566 A | 6/1994 | Miller | 606/60 |
| 5,395,374 A | 3/1995 | Miller et al. | 606/74 |
| 5,413,585 A | 5/1995 | Pagedas | 606/232 |
| 5,423,820 A | 6/1995 | Miller et al. | 606/74 |
| 5,500,018 A | 3/1996 | Spotorno et al. | 623/11 |
| 5,568,865 A | 10/1996 | Mase et al. | 206/438 |
| 5,649,927 A | 7/1997 | Kilpela et al. | 606/74 |
| 5,653,711 A | 8/1997 | Hayano et al. | 606/74 |
| 5,702,399 A | 12/1997 | Kilpela et al. | 606/72 |
| 5,720,747 A | 2/1998 | Burke | 606/74 |
| 5,741,259 A | 4/1998 | Chan | 606/74 |
| 5,772,663 A | 6/1998 | Whiteside et al. | 606/74 |
| 5,794,914 A | * 8/1998 | Woodward | 248/317 |
| 5,810,825 A | 9/1998 | Huebner | 606/74 |
| 5,868,748 A | 2/1999 | Burke | 606/74 |
| 5,908,421 A | 6/1999 | Beger | 606/61 |
| 5,928,237 A | 7/1999 | Farris et al. | 606/74 |
| 6,017,347 A | 1/2000 | Huebner et al. | 606/74 |

FOREIGN PATENT DOCUMENTS

| | | |
|---|---|---|
| WO | WO 94/28812 | 12/1994 |
| WO | WO 95/22294 | 8/1995 |

* cited by examiner

*Primary Examiner*—David O. Reip
*Assistant Examiner*—Julian W. Woo
(74) *Attorney, Agent, or Firm*—Pennie & Edmonds LLP

(57) ABSTRACT

A surgical cable crimp device including a cable with a fixed and a free end and a crimp member for securing the cable. The crimp member has a first leg having a blind hole for receiving the fixed end of the cable, and a second leg with a through bore extending through the second leg for receiving the free end of the cable, the first and second legs connected in the front by a front bridging portion and in the back by a rear bridging portion. The rear bridging portion is longer than the front bridging portion so that the crimp member has a wedge-shape and the second leg is crimpable so that the cable is crimped to the crimp member after the free end is inserted in the through bore.

15 Claims, 14 Drawing Sheets

SURGICAL CABLE CRIMP

FIELD OF THE INVENTION

The present invention is directed to an orthopedic instrument in general, and in particular to a fastening or crimping device for use with surgical cables in fixation of bones during surgeries for fractured bone or bone reconstruction.

BACKGROUND OF THE INVENTION

In surgical and orthopedic operative techniques, it is frequently necessary to fix bone parts, which have been separated surgically or because of fracture, in an exact mutual position and to join them together under pressure. Surgical cable and crimp assemblies are frequently used for this purpose. The cables are used to encircle the bone, or bone and plate, to provide for fixation. In fixation by cable, it is customary to use a fastening device, typically a crimp device which is adapted to be deformed upon the cable for securing the cable in place, encircling the bone in the fracture area. Such assemblies can be subjected to very high tensile forces when, for example, the fractured bone is subjected to a high bending moment. It is therefore important that the cable and crimp assembly have sufficient strength to prevent cable failure under tensile force.

Typically, the cable must be used in a subcutaneous confined area. Thus it is important that the cable and crimp assembly be easy to assemble in such a restricted area. For instance it is desirable to have a device which allows the cable to pass easily through the crimp member to prevent kinking and possible fraying of the cable where it enters the crimp member. Also it is advantageous to have easy access to the crimp device to facilitate crimping. Easy cable access is also desirable to provide room for the application of a tension tool to tighten the cable around the bone. Furthermore, it is desirable to maintain the bulk of the cable as well as the joint where the cable is affixed to itself as compact as possible to minimize discomfort to the patient and damage to the surrounding tissue.

A wide variety of devices for crimping a surgical wire are known in the art. Examples of such crimp devices include those described in U.S. Pat. No. 5,810,825 issued to Huebner, U.S. Pat. Nos. 5,868,748 and 5,720,747 to Burke. Although these devices are quite successful from a technical point-of-view in achieving the desired crimping of surgical wire, most of existing devices have practical limitations. For example, most crimping devices maintain the surgical wire or cable parallel to itself in the fastening or crimping member which makes it difficult to access the free end of the cable and tighten around the bone. In addition, some crimping devices require that the entire fastening or crimping member be crimped in order to secure the surgical wire thereto, necessitating a larger access area to permit a crimping tool to access the entire fastening or crimping member.

Other crimp devices exist which are substantially "L" shaped and maintain the surgical wire or cable at a 90° angle to itself as it leaves the fastening or crimping member. Maintaining the cable at such a steep angle can put a kink in the cable at that location and increase the likelihood that the cable will break. Furthermore, when the crimping member maintains the cable at a 90° angle, it is more difficult to insert the cable through the crimp member.

Thus, there exists a need for an improved surgical crimp device that is compact, sufficiently strong, and easy to assemble in a confined area.

SUMMARY OF THE INVENTION

The present invention is directed to a surgical fastener device for fixing bone elements comprising a flexible cable having first and second ends attached to a crimp member. The crimp member has first and second portions extending between front and rear ends. First and second portions are spaced farthest apart at the rear end to form a wedge-shaped. Additionally, a channel extends through the second portion. The first end of the cable is fixedly secured to the first portion at the rear end, and the second end of the cable is insertable through the channel of the second portion for forming a loop of adjustable diameter.

In one embodiment, the front and rear ends of the crimp member are rounded and the front end of the crimp member can have a smaller arc length than the rear end.

In another embodiment, the front end of the crimp member is solid and the rear end has a longitudinal slot.

In yet another embodiment, the crimp member has an open central portion that forms a substantially triangular cutout.

In an alternative embodiment, the second end of the cable has a leader to facilitate handling.

In an additional embodiment, the cable is multi-stranded.

In another embodiment, the first and second portions of the crimp member are coplanar.

The present invention is further directed to a surgical fastener device for crimping surgical cable. The device includes a crimp member comprising a wedge-like body having first and second parallel major surfaces vertically interconnected by a peripheral edge. The body has a centrally disposed triangular opening vertically extending through the body from the first major surface to the second major surface. The body also has a pair of channels extending longitudinally through the body. The channels are disposed at a non-parallel angle with respect to each other.

In an alternative embodiment, the device further includes a flexible cable secured to one of the channels of the crimp member. The cable has first and second ends and one end is fixedly attached to the crimp member and the other end is insertable through the other channel for forming a loop of adjustable diameter. The cable can be multi-stranded and the insertable end can have a leader to facilitate handling.

The present invention is also directed to a surgical fastening device comprising a cable having a free end and a fixed end attached to a crimp member. The crimp member has a first leg with first and second ends. The first end has a blind hole for receiving the fixed end of the cable. The crimp member also has a second leg with first and second ends. The second leg has a through bore extending from the first end to the second end of the second leg. The crimp member also has a front bridging portion connecting the second end of the first leg to the second end of the second leg. The crimp member also has a rear bridging portion connecting the first end of the first leg to the first end of the second leg. The rear bridging portion is longer than the front bridging portion so that the crimp member has a wedge-shape. The second leg is crimpable so that the cable is crimped to the crimp member after the free end is inserted in the through bore.

In another embodiment, the cable is multi-stranded and the free end has a leader to facilitate handling.

DESCRIPTION OF THE PREFERRED EMBODIMENTS

Figure 1:
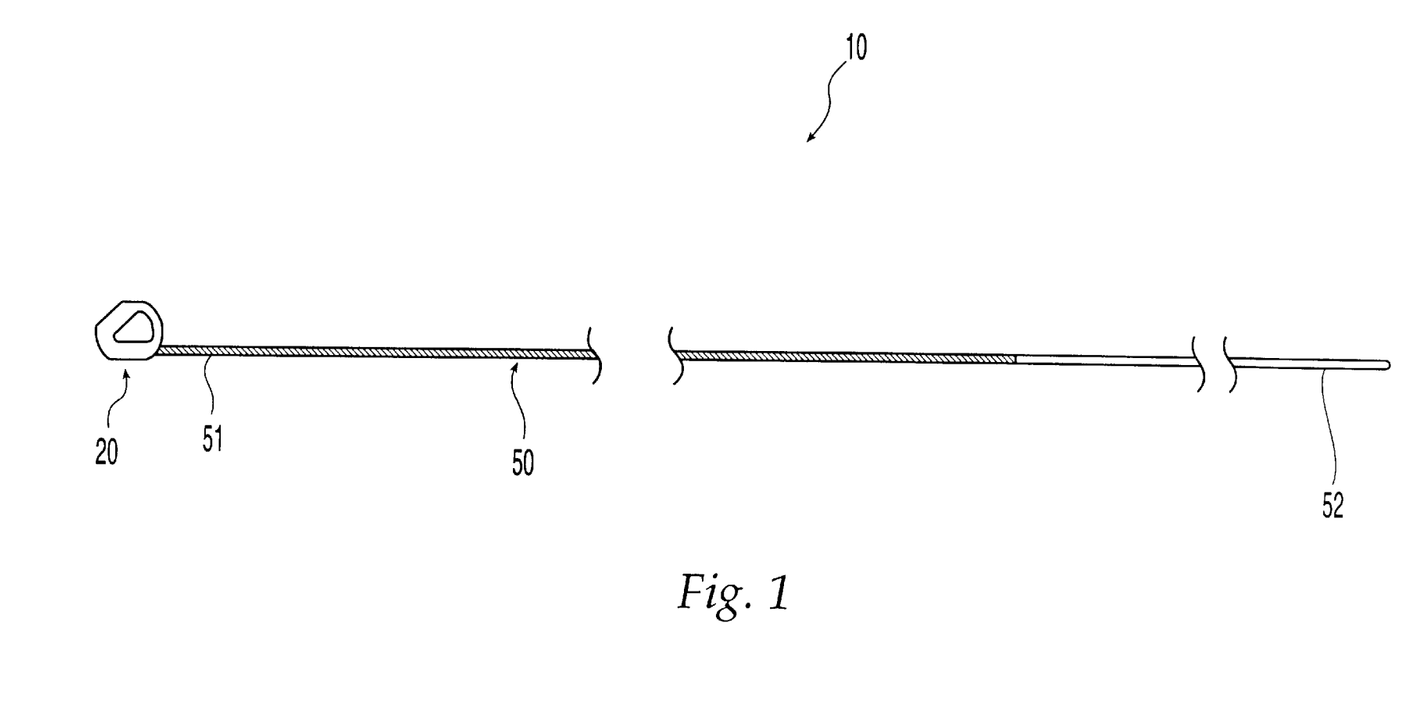
FIG. 1 is a top view of a surgical crimp device according to the present invention showing a flexible cable and a crimp member.
Figure 2:
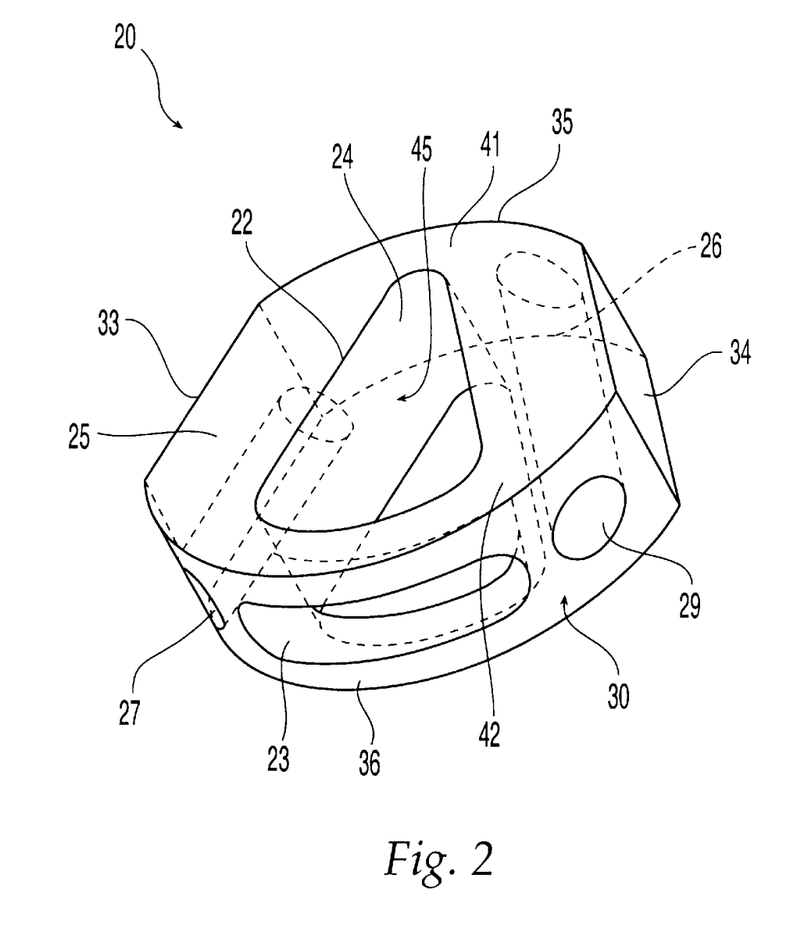
FIG. 2 is a perspective view of the crimp member of FIG. 1 prior to assembly with the cable.

As shown in FIG. 1, a surgical crimp device 10 according to the present invention includes a crimp member 20 and a flexible cable 50. Cable 50 can be either a single strand wire or a multi-wire stranded cable. A first end 51 of the cable is fixedly attached to crimp member 20 and a second end 52 of the cable is a free end.

As best seen in FIGS. 2–5, crimp member 20 preferably has a wedge-shape with a generally triangular perimeter. For ease in handling, the corners are rounded or smoothed rather than meeting at sharp points. The crimp member preferably has a planar top surface 31, a spaced parallel planar bottom surface 32, and a perimeter surface 30 extending vertically therebetween. Perimeter surface 30 has two sidewall sections 33 and 34, a front wall section 35, and a base wall section 36. Sidewall sections 33 and 34 are displaced at a non-parallel angle with respect to each other. Preferably sidewall sections 33 and 34 are at an acute angle with respect to each other. Sidewall sections 33 and 34 are connected by a rounded front wall section 35 at the front end or vertex. At the back end or base, the two sidewall sections are connected by a rounded base wall section 36. The rounded base wall section preferably has a larger radius of curvature than front wall section 35.

Crimp member 20 preferably has a vertical cutout 24. In the preferred embodiment vertical cutout 24 is generally triangular. Preferably cutout perimeter surface 45 is similar to the crimp member perimeter surface 30 such that cutout 24 has side sections 37 and 38 which are parallel to the perimeter sidewall sections 33 and 34 respectively. The cutout side sections are connected at the front end or apex by a rounded front section 39 and at the back end or base by a rounded base section 40. The rounded base section 40 of the cutout preferably has a larger radius of curvature than the front section 39.

In the embodiment shown in FIGS. 2–5, cutout side section 37 and perimeter sidewall section 33 together define a first leg 25. Cutout side section 38 and perimeter sidewall section 34 together define a second leg 26. Cutout front section 39 and perimeter front wall section 35 together define a nose section 41. Cutout base section 40 and perimeter base wall section 36 together define a bridge section 42. Nose section 41 at the front end is preferably solid and bridge section 42 at the back end preferably has a longitudinal slot 23 extending therethrough. Thus, crimp member 20 has first leg 25 and second leg 26 which are attached at the front end by nose section 41 and extend longitudinally from the front end of crimp member 20 to the back end or base at a non-parallel, preferably acute, angle. First and second legs 25, 26 are spaced farthest apart at the back end. First and second legs 25, 26 are horizontally connected at the back end by bridge section 42.

Figure 3:
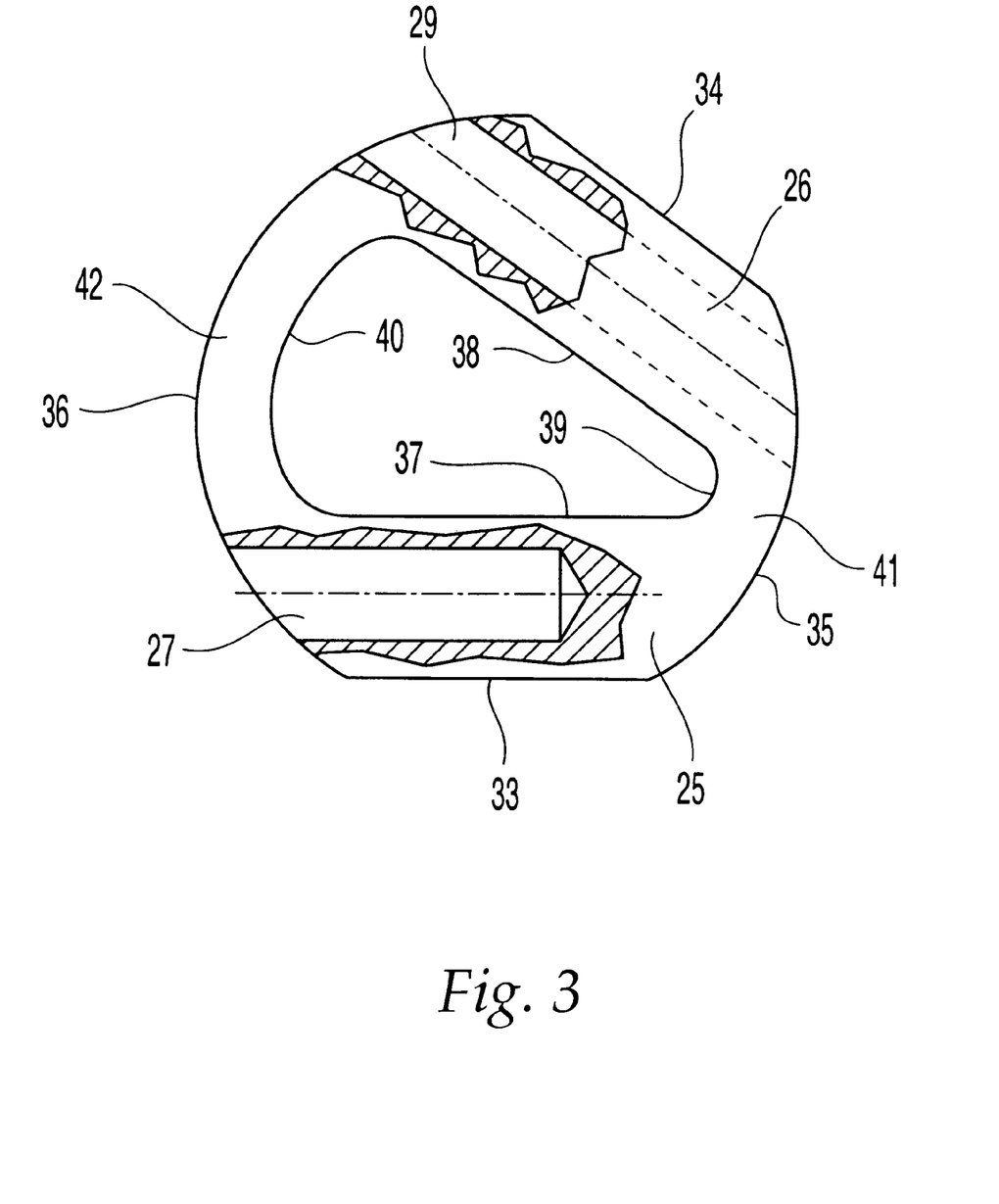
FIG. 3 is a top view of the crimp member of FIG. 2 with a cutaway showing cross sections of internal channels therein.
Figure 4:
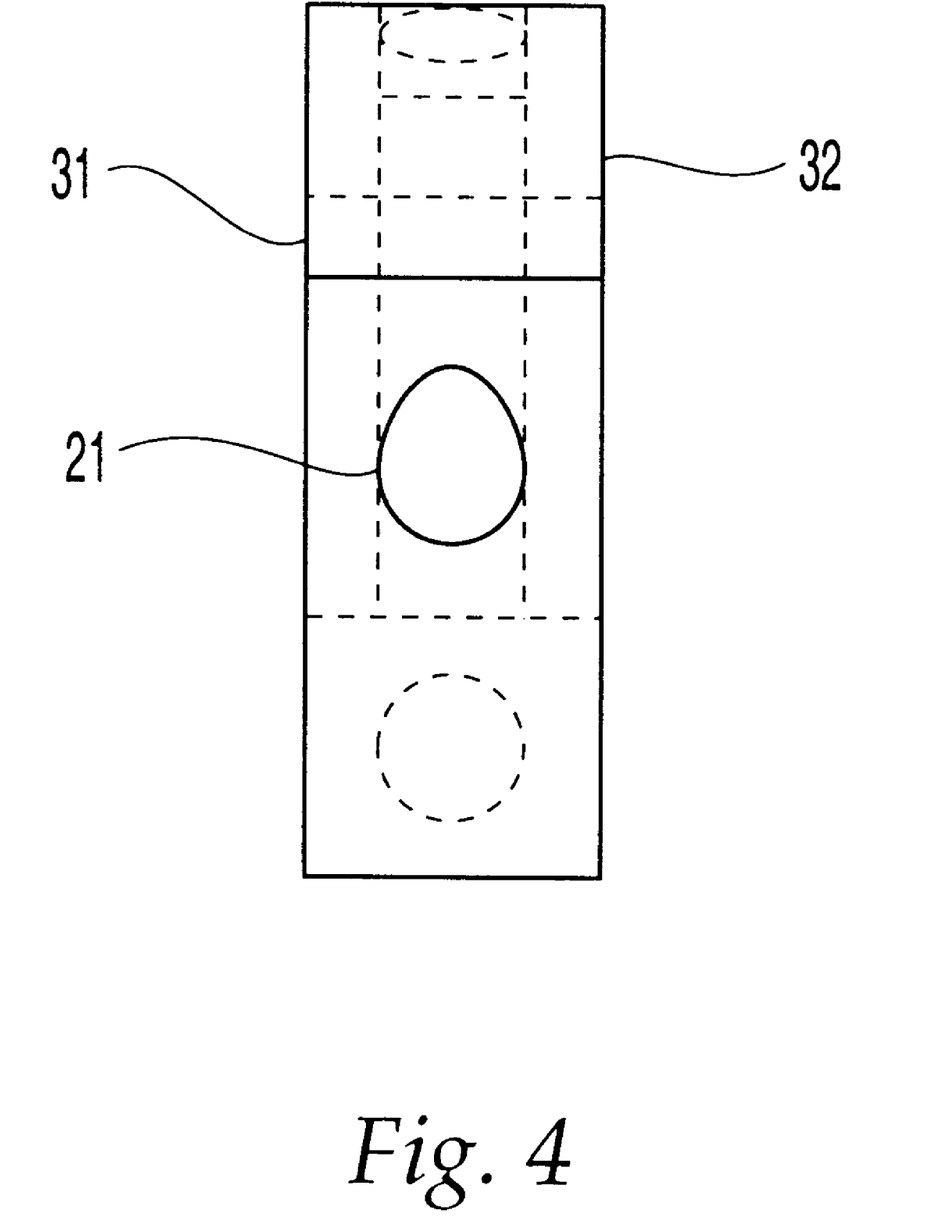
FIG. 4 is a front view of the crimp member of FIG. 2.
Figure 5:
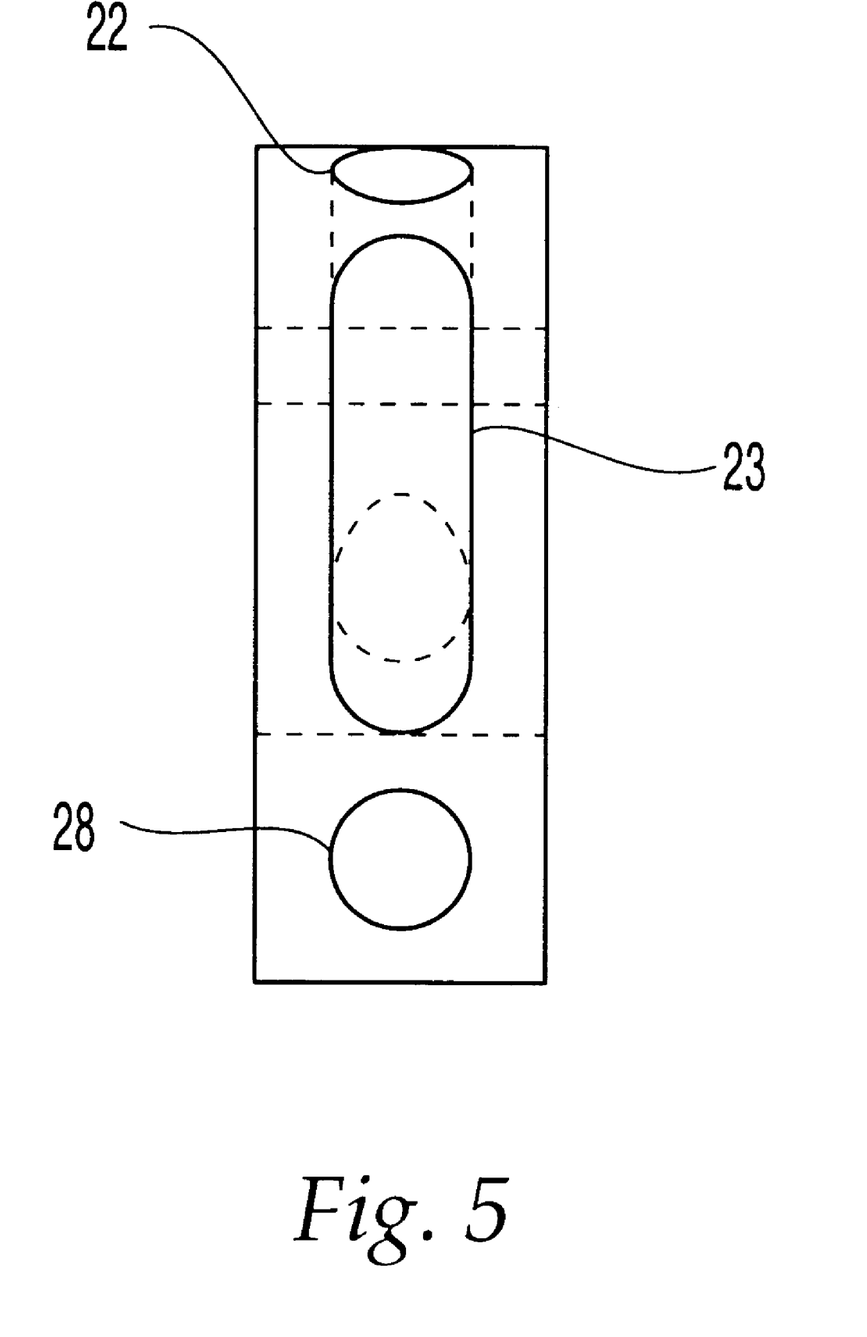
FIG. 5 is a back view of the crimp member of FIG. 2.

First leg 25 has an internal blind channel 27 extending longitudinally therein for receiving first end 51 of cable 50. Channel 27 preferably has one opening located at perimeter base wall section 36 located at the back end of crimp member 20. Preferably blind channel 27 is cylindrical with a longitudinally extending central axis parallel with perimeter sidewall section 33 and cutout side section 37. Second leg 26 has a through channel 29 for receiving second end 52 of cable 50, which extends longitudinally through the entire second leg. Through channel 29 has a front opening 21 at perimeter front wall section 35 and a base opening 22 at the perimeter base wall portion 36. Preferably, through channel 29 is cylindrical with a longitudinally extending central axis disposed parallel to perimeter sidewall section 34 and side section 38 of vertical cutout 24. In FIG. 3, portions of crimp member 20 are broken away to show the internal channels 27 and 29 of the first leg 25 and second leg 26 respectively. The longitudinally extending central axes of these channels are coplanar. First and second legs 25 and 26 have a thickness slightly larger than the diameter of cable 50 so as to allow cable 50 to be inserted therethrough.

Figure 6:
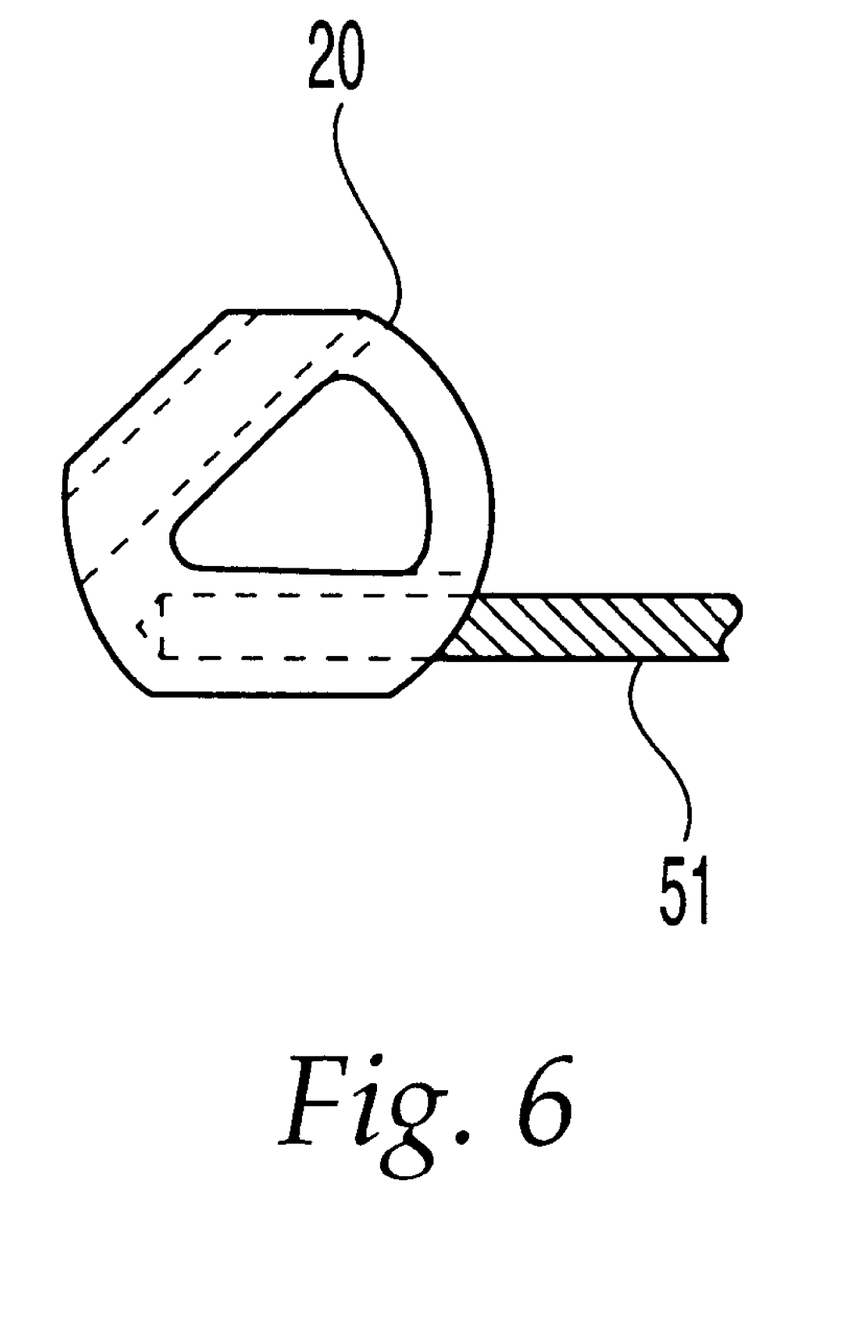
FIG. 6 is a magnified view of FIG. 1 with an enlargement of the first end of the cable.

Referring to FIG. 6, first end 51 of cable 50 is fixedly attached to crimp member 20. Any suitable means for securing first end 51 of cable 50 to crimp member 20 can be used, such as gluing, welding, swaging, etc. Preferably, first end 51 of cable 50 is inserted in blind channel 27 of first leg 25 and cable 50 is swaged to the channel to permanently secure first end 51 of cable 50 to crimp member 20. Second end 52 of cable 50 has a leader portion 53 welded thereto to facilitate handling of cable 50 and entrance of second end 52 into through channel 29 of second leg 26 during operation.

Figure 7:
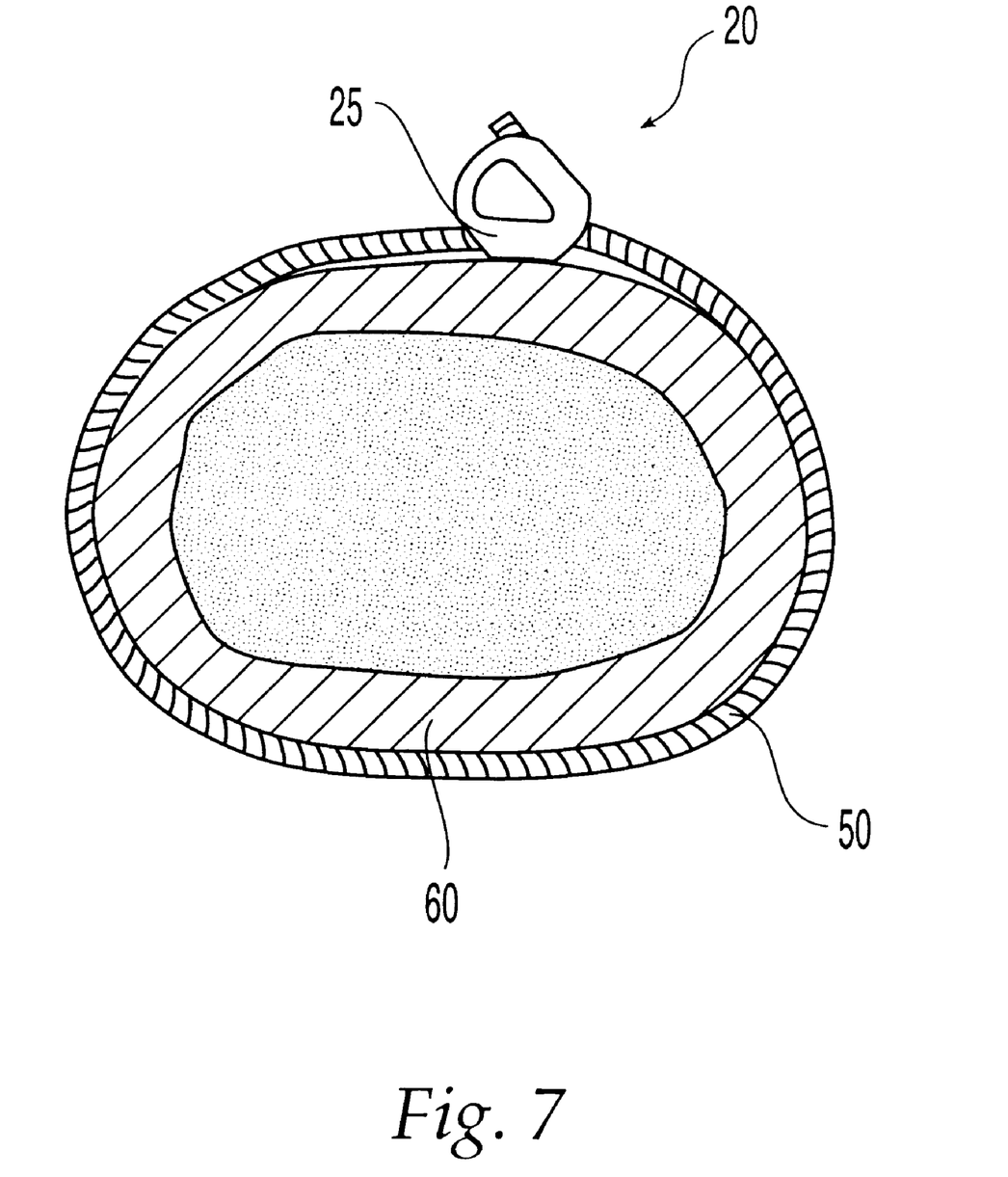
FIG. 7 is a side view of the surgical crimp device of FIG. 1 after the device has been crimped around a bone.
Figure 8:
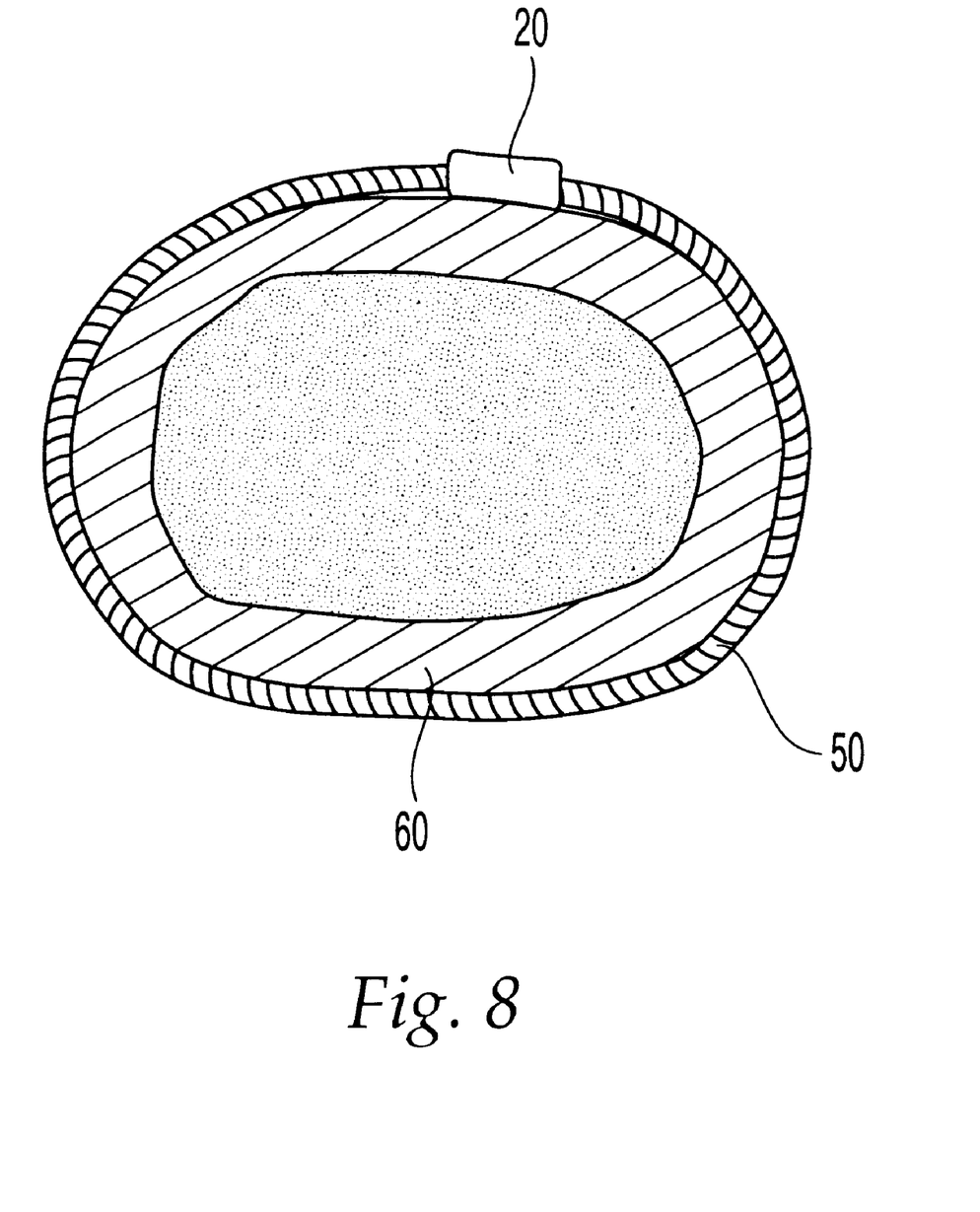
FIG. 8 is a side view of the surgical crimp device of FIG. 7 showing the crimp member in a low profile position.
Figure 9:
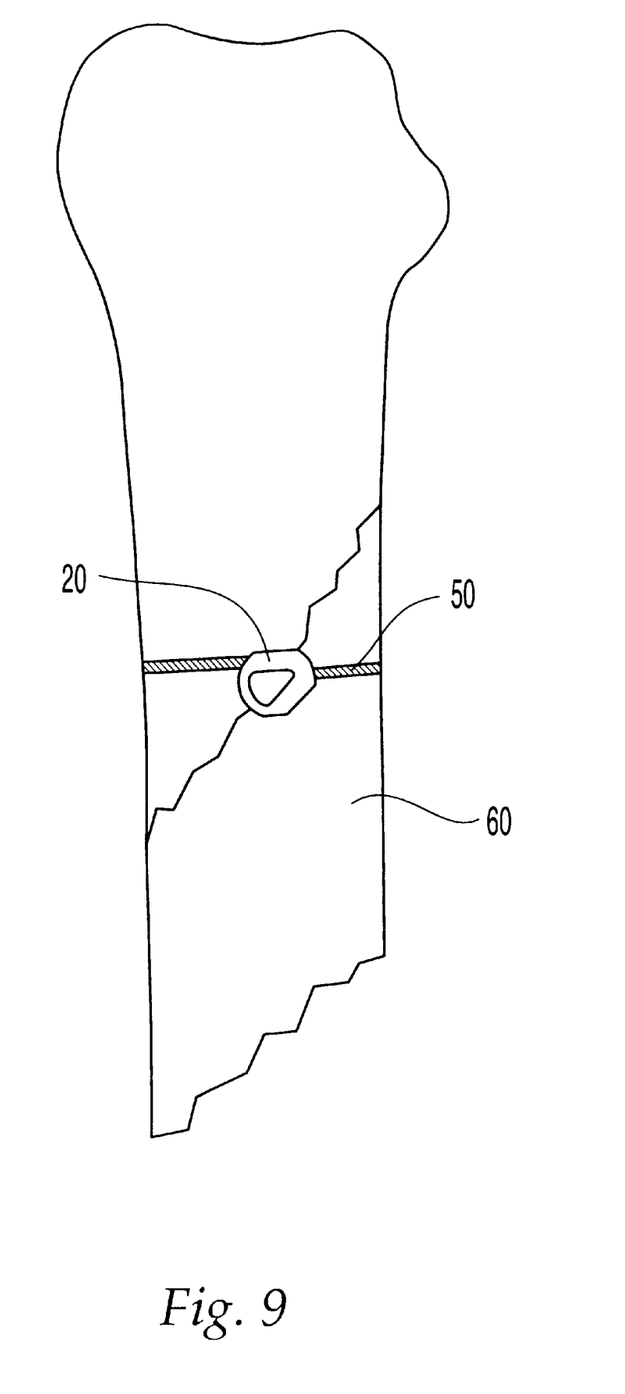
FIG. 9 is a top view of the surgical crimp device of FIG. 8.

In order to use the surgical crimp device to secure a cable around a bone, the surgeon first prepares the area by exposing the patient's bone. Referring to FIGS. 7–9, the crimp member is placed against a bone 60 to be mended and second end 52 of the cable is wrapped around bone 60. Second end 52 of cable 50 is then inserted in through channel 29 of crimp member 20. The cable preferably enters channel 29 through front opening 21 and exits channel 29 through base opening 22, however, the cable can be inserted in through channel 29 in a reverse manner. Initially sidewall section 33 is preferably placed tangent to bone 60 so that crimp member 20 is resting on first leg 25 and second leg 26 is angled away from bone 60. When cable 50 is inserted in through channel 29 and second end 52 exits base opening 22, second end 52 is angled away from bone 60 and toward a surgeon allowing the cable to angle away from the bone is particularly advantageous because second end 52 is easier to access by a tensioning tool. Second end 52 of cable 50 is then pulled to bring cable 50 taut around bone 60 with the aid of a conventional tensioning tool which is not shown in the drawings. When the desired tension is achieved, second leg 26 is crushed with pliers or a similar crimping instrument as are known in the art. It is particularly advantageous that second leg 26 is angled away from bone 60 to allow greater access for a crimping instrument in a confined area. In addition, because only a portion of crimp member 20 is crushed, here second leg 26, less force is required than crushing the entire crimp member. When second leg 26 is crushed, through channel 29 is deformed or constricted, preventing movement of cable 50 therethrough to secure the cable within through channel 29 under tension. Any excess cable that extends beyond the back end can then be cut and removed.

As shown in FIGS. 8 and 9, crimp member 20 can be pushed over to lay flat after crimping second leg 26, placing either top planar surface 31 or bottom planar surface 32 in contact with bone 60. As a result, the profile of the crimp device in the body is reduced. For example, after legs 25 and 26 are crimped and crimp member 20 is pushed over to lay flat, the resulting thickness of crimp member 20 is preferably not substantially thicker than the radius of cable 50.

Although cable 50 is shown as a multi-strand wire, the invention can be used with any type of surgical cable, such as a single strand wire. Preferably, the cable used with the proposed crimp is a multi-wire stranded cable. Crimp member 20 and cable 50 are preferably titanium although they may be manufactured from any material suitable for surgical procedures.

Figure 10:
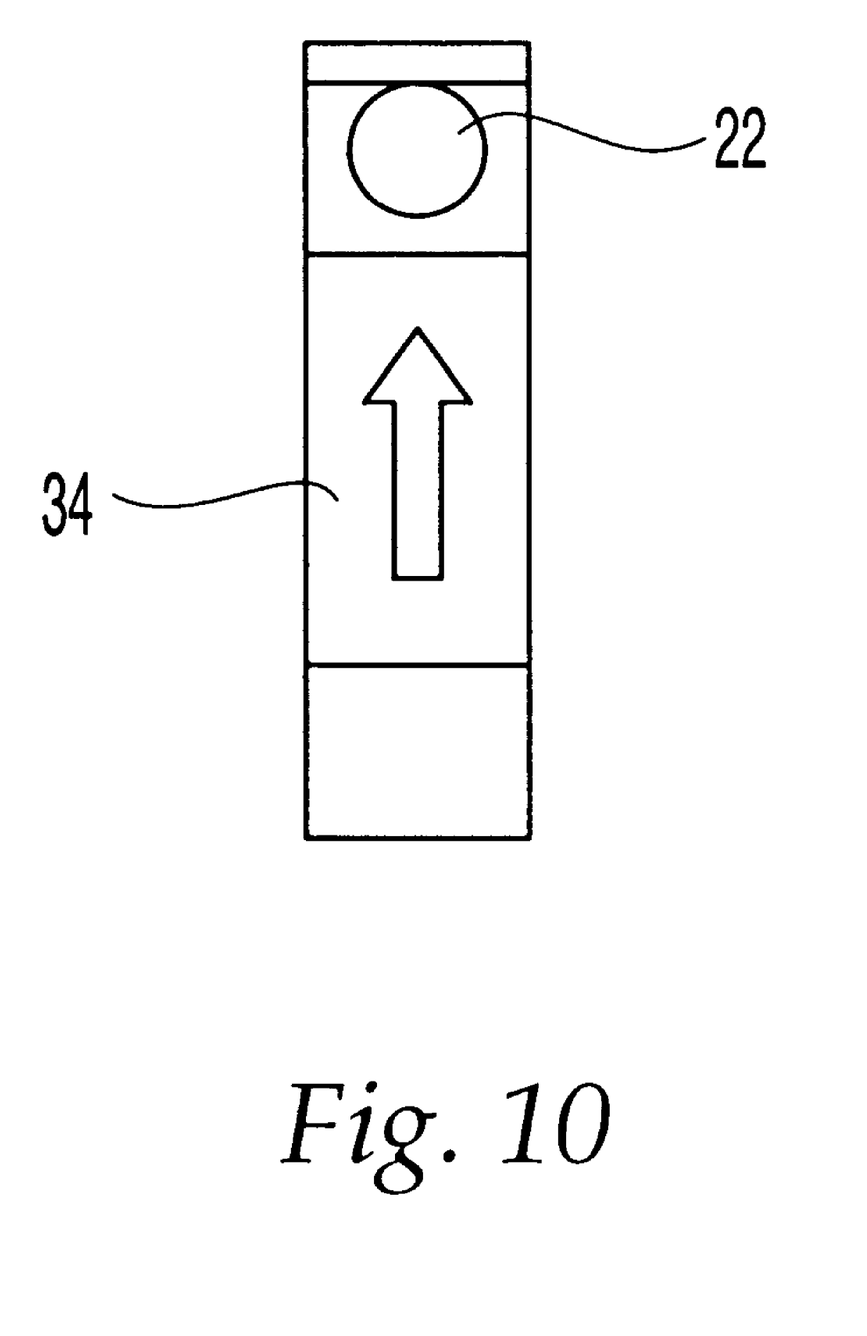
FIG. 10 is a side view of the crimp member of FIG. 2.

Referring to FIG. 10, preferably an arrow, symbol or other indicia is etched on the outside of the second leg to illustrate the preferred direction to insert second end 52 of cable 50 in the through channel 29.

Figure 11:
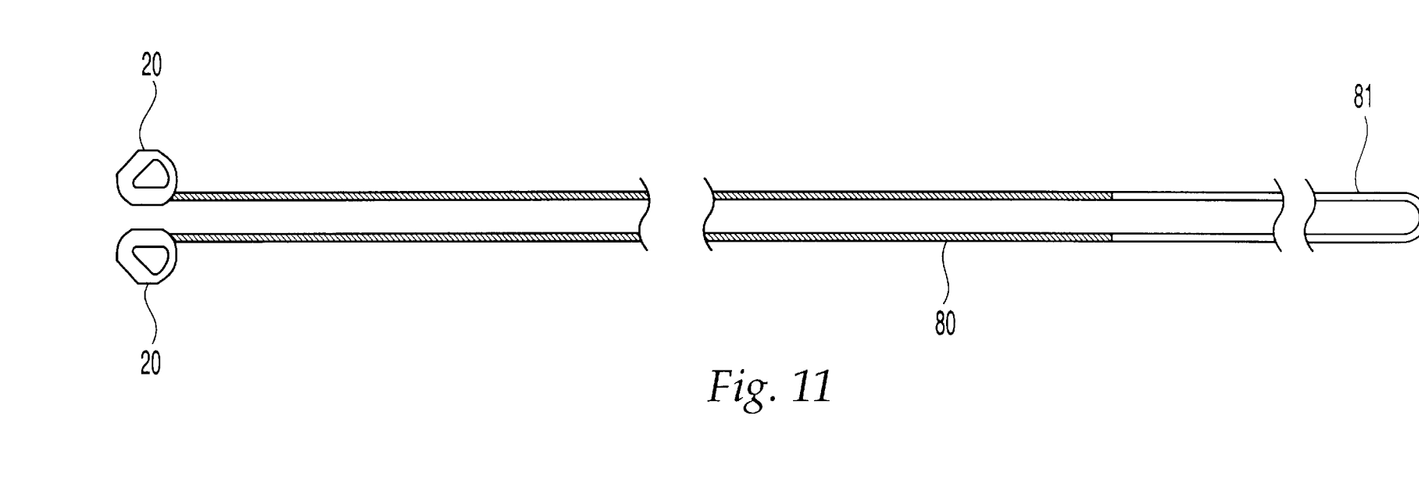
FIG. 11 a top view of an alternative embodiment of the surgical crimp device.

Referring to FIG. 11, another embodiment of the present invention includes a cable 80 having a crimp member as previously described attached on each end. A leader portion 81 is welded onto the cable at the longitudinal center of the cable. When a crimp device, cable 80 is cut in the center of leader portion 81 to yield two identical crimp devices according to the present invention. This embodiment of the present invention provides for efficient manufacturing and storage of the crimp devices.

Figure 12:
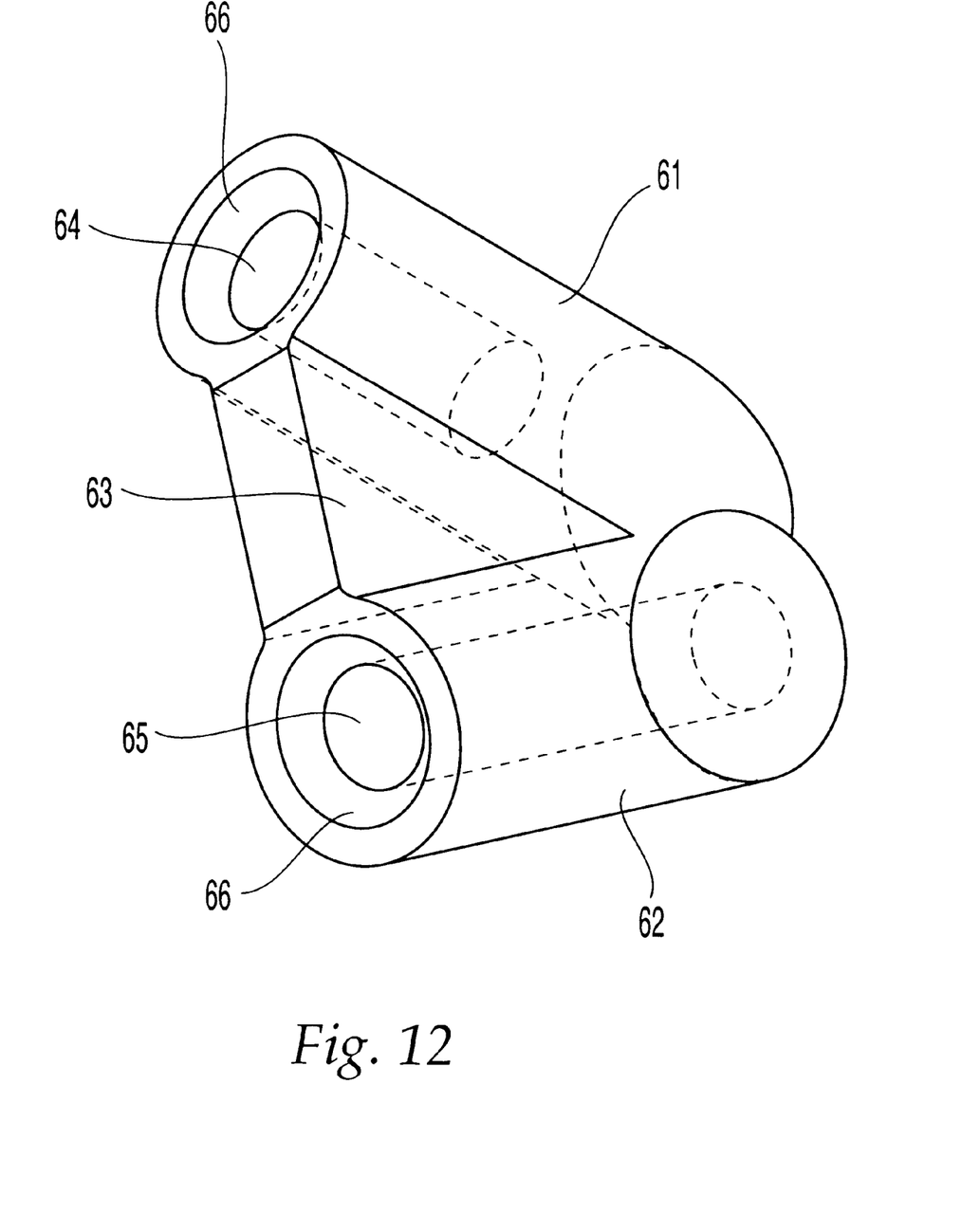
FIG. 12 is a perspective view of an alternative embodiment of the crimp member.
Figure 13:
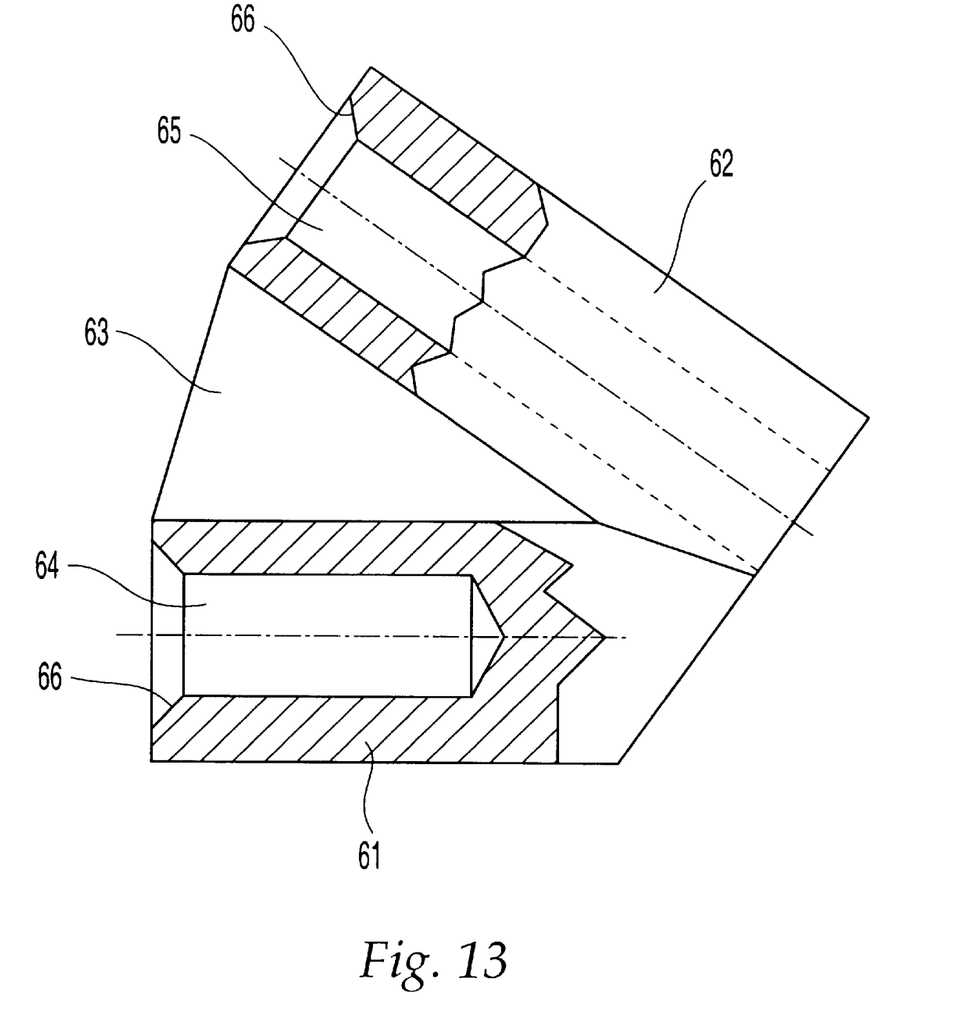
FIG. 13 is a top view of the crimp member of FIG. 9 with a cutaway showing cross sections of the internal channels therein.
Figure 14:
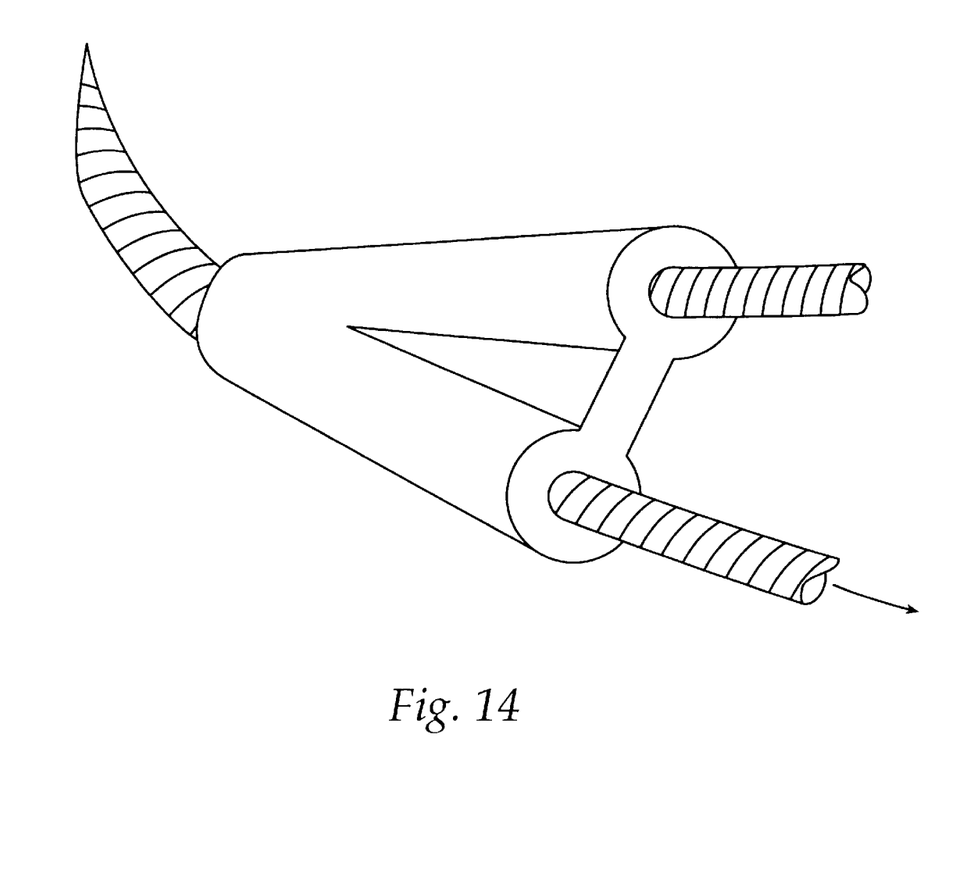
FIG. 14 is a perspective view of the crimp member of FIG. 9 showing a cable extending therethrough.

Referring now to FIGS. 12–14, an alternative embodiment of the crimp member has two leg members, first leg 61 and second leg 62, arranged in a generally triangular configuration and attached at the front end or vertex. Leg members 61 and 62 are preferably displaced at a non parallel angle with respect to each other. Preferably leg members 61 and 62 are displaced at an acute angle with respect to one another. Legs 61 and 62 are connected horizontally by a web section 63. In this embodiment, legs 61 and 62 are substantially cylindrical with concentric channels therein. First leg 61 has a blind concentric channel 64 extending longitudinally therein. Blind channel 64 has one opening at the back end of the crimp member. Second leg 62 has a concentric through channel 65 extending through the entire length of leg 62. Through channel 65 has one opening at the back end and one opening at the front end. A conical chamfer 66 surrounds the openings of channels 64, 65 to guide the entrance of the cable into the channels.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A surgical fastener device for fixing bone elements comprising:

a flexible cable having first and second ends; and a crimp member having first and second portions and extending between front and rear ends with said first and second portions spaced farthest apart at the rear end to form a wedge-shape, wherein the front and rear ends are rounded, and said second portion having a channel extending there through, wherein the first end of the cable is fixedly secured to said first portion at the rear end and the second end of the cable is insertable through the channel of the second portion for forming a loop of adjustable diameter.

2. The device according to claim 1 wherein the front end of the crimp member is solid and the rear end has a longitudinal slot.

3. The device according to claim 1 wherein the front end of the crimp member is solid and the rear end has a longitudinal slot.

4. The device according to claim 1 wherein the crimp member has an open central portion that forms a substantially triangular cutout.

5. The device according to claim 1 wherein the second end of the cable has a leader to facilitate handling.

6. The device according to claim 1 wherein the cable is multi-stranded.

7. The device according to claim 1 wherein the first and second portions of the crimp member are coplanar.

8. A surgical fastener device for crimping surgical cable, said device including a crimp member comprising a wedge-like body having first and second parallel major surfaces vertically interconnected by a peripheral edge, said body having a centrally disposed triangular opening vertically extending through said body from the first major surface to the second major surface and a pair of channels extending longitudinally through said body, said channels being disposed at a non-parallel angle with respect to each other.

9. The device of claim 8 further comprising a flexible cable having first and second ends, one of which is fixedly secured to one of the channels of the crimp member, and the other of which is insertable through the other channel for forming a loop of adjustable diameter.

10. The device of claim 9 wherein the cable is multi-stranded and the insertable end has a leader to facilitate handling.

11. The device according to claim 8 wherein the crimp member is movable to a position wherein at least one of the major surfaces contacts the bone.

12. A surgical fastening device comprising a cable having free and fixed ends, and a crimp member comprising:

a first leg with first and second ends, the first end having a blind hole for receiving the fixed end of the cable, a second leg with first and second ends and a through bore extending from the first end to the second end of the second leg, a front bridging portion having a radius of curvature and connecting the second end of the first leg to the second end of the second leg, and a rear bridging portion having a radius of curvature and connecting the first end of the first leg to the first end of the second leg, wherein:

the rear bridging portion is longer than the front bridging portion so that the crimp member has a wedge-shape and the second leg is crimpable so that the cable is crimped to the crimp member after the free end is inserted in the through bore.

13. The device of claim 12 wherein the cable is multi-stranded and the free end has a leader to facilitate handling.

14. A surgical fastener device for fixing bone elements comprising: a flexible cable having first and second ends; and a crimp member having first and second portions and extending between front and rear ends with said first and second portions spaced farthest apart at the rear end to form a wedge-shape, and said second portion having a channel extending there through, wherein the first end of the cable is fixedly secured to said first portion at the rear end and the second end of the cable is insertable through the channel of the second portion for forming a loop of adjustable diameter; wherein the front end of the crimp member is solid and the rear end has a longitudinal slot.

15. The device according to claim 14 wherein the crimp member has an open central portion that forms a substantially triangular cutout.

* * * * *